(12) United States Patent (10) Patent No.: US 7,981,121 B2
Stegfeldt et al. (45) Date of Patent: Jul. 19, 2011

(54) TOOL AND A METHOD FOR ATTACHING A CARDIAC STIMULATOR LEAD AT A DESIRED POSITION INSIDE A HEART

(75) Inventors: Olof Stegfeldt, Älta (SE); Rolf Hill, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 682 days.

(21) Appl. No.: 11/996,527

(22) PCT Filed: Aug. 22, 2005

(86) PCT No.: PCT/SE2005/001223
§ 371 (c)(1),
(2), (4) Date: Jan. 23, 2008

(87) PCT Pub. No.: WO2007/024160
PCT Pub. Date: Mar. 1, 2007

(65) Prior Publication Data
US 2008/0234694 A1 Sep. 25, 2008

(51) Int. Cl.
*A61B 19/00* (2006.01)
(52) U.S. Cl. .......................... 606/129; 607/122
(58) Field of Classification Search .................. 606/108, 606/139, 144, 148; 607/127, 126, 115, 116, 607/119, 122; 623/1.36
See application file for complete search history.

(56) References Cited

U.S. PATENT DOCUMENTS

| 5,514,173 A | 5/1996 | Rebell et al. |
| 7,096,071 B2 | 8/2006 | Ollivier et al. |
| 7,491,232 B2 * | 2/2009 | Bolduc et al. ................ 623/1.36 |

FOREIGN PATENT DOCUMENTS

| EP | 0 113 253 | 7/1984 |
| GB | 1 560 411 | 2/1980 |

* cited by examiner

*Primary Examiner* — Tuan V. Nguyen
(74) *Attorney, Agent, or Firm* — Schiff Hardin LLP

(57) ABSTRACT

For attaching a cardiac stimulator lead at a desired position inside a heart, the stimulator lead having a flexible tube from which a helix is extendible at a distal end thereof by a screw rotating motion and having a proximal end interconnected with an operating member, a tool has a flexible portion wire with an engagement formation at a distal end thereof that mates with a complimentary engagement formation at a proximal end of the operating member. The tool has a handle containing an internal cavity, with a proximal portion of the torsion wire being rotationally rotated by the handle in the internal cavity, and a resilient yoke is formed in the internal cavity, with at least a part of the yoke engaging grooves and ridges in a circumferential boundary surface of the internal cavity.

4 Claims, 4 Drawing Sheets

TOOL AND A METHOD FOR ATTACHING A CARDIAC STIMULATOR LEAD AT A DESIRED POSITION INSIDE A HEART

FIELD OF THE INVENTION

The present invention relates to a tool for attaching a cardiac stimulator lead at a desired position inside a heart, the stimulator lead being of the type which is formed as a flexible tube comprising electrical conductors and a helix, which is extendable out of a distal end of the tube by a screw rotating motion, for penetration into and hence attachment at the desired position, and which, in its proximal end, is interconnected with an operating member, the tool comprising a flexible torsion wire, having an engagement formation in a distal end, and being insertable into the cardiac stimulator lead, to effect the screw rotating motion of the operating member by rotating the torsion wire when the engagement formation in the distal end of the torsion wire is in engagement with a mating engagement formation in a proximal end of the operating member.

The invention also relates to a method for attaching of such a cardiac stimulator lead at a desired position inside a heart.

DESCRIPTION OF THE PRIOR ART

It is well known in the art to attach a cardiac stimulator lead inside a heart by means of a corkscrew formed helix, which is rotational extendable from the distal end of the lead for penetration into the heart wall. This is done on some patients for stimulating the heart function by means of signals from a pacemaker via the lead. When attaching a cardiac stimulator lead in such a way, it is important that the torsional force exerted on the helix is sufficient to ensure proper attachment to the heart wall. However, it is also important that the exerted torsional force is not too large, in which case there is a risk that the helix will penetrate completely through the heart wall or the entire lead will penetrate into the heart wall.

As used herein, the term distal is used for an end or a portion of an object which is, or is adapted to be situated closest to the heart of a patient. As a logical consequence, the corresponding term proximal is used for an end or a portion of an object which is, or is adapted to be situated furthest away from the heart Some prior art cardiac stimulator leads are of a type comprising a flexible tube of a helically wound metal wire, which is rotatable inside the lead. Then the helically wire can be utilized to carry out the screw rotating motion of the helix. Since the metal wire is helically wound, a large torsional elasticity exists in it, which restricts the maximum torsional force that is possible to transmit via the helical wire. However, this type of lead often experience problems due to excessive friction between the helical wire and the protecting cover, which may lead to jamming. These problems are increasing as the developments in the art goes towards thinner leads, which result in increasing frictional problems between the helical wire and the cover.

Due to these reasons, among others, a new method for attaching the cardiac stimulator lead inside the heart has been developed. In this alternative embodiment, the helical wire can be dispensed with but could also remain to have alternatives for screw rotating the helix. The tip of the lead, embodying may then be guided to a suitable position inside the heart by means of for example a curved, elastic tube which is inserted into the bore of the lead and twisted such that the tip of the lead will pivot. Subsequently, a flexible torsion wire inserted into the flexible tube and having an engagement formation in its distal end, may be used to rotate the helix by engagement into a mating engagement formation in a proximal end of the helix or, more preferably, an operating member, by means of which the helix may be screw rotated out of the tip.

However, when using such a torsion wire for screw rotating the helix, no torque limiting mechanism is incorporated in the system, as in the embodiment having a helically wound wire. Accordingly, the doctor is therefore often obliged to count the number of revolutions made by the torsion wire. This method is however unreliable and may lead to mistakes by e.g. miscounting of the number of revolutions.

Also, when using a curved, elastic tube for guiding the tip of the cardiac stimulator to the proper position inside the heart, it is often necessary to guide and hold the tip in position at the same time as the torsion wire is operated for rotating the helix.

SUMMARY OF THE INVENTION

It is an object of the invention to eliminate at least some of the above disadvantages and provide a simple, inexpensive and reliable tool for limiting the torque transmitted to the helix when attaching a cardiac stimulator lead to a heart wall.

Accordingly, the basis of the invention is the insight that there is a need for a torque limiter, which prevents further rotating of the helix when a sufficient length has been screwed out from the tip, and which prevents twisting of the entire lead. However, such a torque limiter should preferably be as inexpensive and uncomplicated as possible, and yet ensure a reliable function, especially since the torque limiter normally will be disposed of after use.

The basis of a second aspect of the invention is the insight that there is also a need for a pressure limiter to restrain the longitudinal force in the torsion wire.

The basis of a third aspect of the invention is the insight that there is also a need for a tool by which it is possible to perform both the rotation of a curved, elastic guide tube, to pivot the tip of the cardiac stimulator lead, as well as the rotation of the torsion wire inside the tube, to perform the screwing in of the helix into the heart wall.

Accordingly, the object is achieved by a tool having a handle having an internal cavity with a generally circular form in cross-section perpendicular to a centre axis, which is extended between a proximal end and a distal end of the cavity, the internal cavity being corrugated in a circumferential boundary surface, having grooves and ridges in parallel to the center axis, wherein a proximal portion of the flexible torsion wire, is rotationally supported by the handle in the proximal end as well as the distal end of the internal cavity in coaxial with the center axis of the internal cavity, and has a resilient yoke formed portion in the internal cavity with at least a part of the yoke in contact and engagement with the grooves and ridges of the circumferential boundary surface.

When performing the screw rotation of the operating member and hence the helix by means of a tool formed in this way, the largest torque which is possible to apply to the helix will be restricted. This is due to the fact that when the torque becomes to large, the yoke portion of the torsion wire inside the cavity, will be deformed such that the yoke portion being in engagement with the grooves and the ridges in the circumferential boundary surface of the cavity, will slide out of engagement with one of the grooves and ratches over the following ridge(s) to the following groove(s) in the cavity.

The size of the torque limit, when the wire yoke ratches over the ridges, may be changed by changing the form and dimension of the various elements in the tool. For example by varying the dimension and length of the yoke portion, the material in the yoke portion, the form of the internal cavity and the form of the grooves and ridges, the torque limit may be regulated.

In a preferred embodiment, the ridges in the internal cavity have a saw tooth-shape, with a sloping flank in the direction in which the screwing of the helix into the heart wall is performed, whereas the ridges in the opposite direction have a steep flank for screwing the helix out from the heart wall, when actually no torque restriction is required. However, the form and dimension of the grooves and ridges may be varied for different purposes.

It is advantageous if the torsion wire, in the distal end is flexible but has no elasticity for reasons of not disturbing the guidance of the tip of the cardiac stimulator lead. On the other hand, in the proximal end, i.e. in the yoke portion, the torsion wire has to be elastic to be able to adapt the proper form but yet be able to be deformed. To achieve such combined characteristics, the torsion wire can be of two different materials which are joined, preferably within the handle. In practice, however, it is usually no big problem if the torsion wire has some elasticity also in the distal end, since the cross sectional dimensions involved are so small, and hence also the forces, and in such cases the torsion wire may be formed in one unitary piece.

When rotating the helix by means of the torsion wire, it is important to press the torsion wire towards the distal end such that proper engagement is ensured between the distal end of the torsion wire and the proximal end of the operating member. It may also be necessary to press the torsion wire towards the distal end to ensure proper abutment of the end of the tip in the cardiac stimulator lead against the heart wall. However, to prevent too much pressure in the longitudinal direction of the torsion wire it is preferred, according to one embodiment of the invention, to support the portion of the torsion wire located in the handle on the distal side of the internal cavity, not only rotatable but also displaceable in the longitudinal direction. In this way is in a simple manner achieved, due to the elastic yoke, a pressure limiter which resilient restrains the maximal longitudinal pressure force in the torsion wire.

In a further preferred embodiment, the tool is especially adapted for the case where the cardiac stimulator lead is guided by means of an elastic guide tube having a curved distal portion, which is inserted into the cardiac stimulator lead and used for pivoting the tip of the cardiac stimulator lead to the desired position by rotating the guide tube at the proximal end. For this reason the handle is divided into two parts, namely a first and a second handle piece, respectively, which are rotatable connected to each other, the first handle piece forming the distal end of the internal cavity, whereas the second handle piece forming the circumferential boundary surface and the proximal end of the internal cavity. In this embodiment the proximal end of the guide tube is torsion resistant connected to the first handle piece, in coaxial with the centre axis of the cavity and on the distal side of the internal cavity. The torsion wire is inserted into the guide tube, has a yoke portion within the internal cavity and is rotationally supported by the second handle piece in coaxial with the centre axis of the internal cavity and in the proximal end thereof. The torsion wire is rotatable and displaceable supported in the guide tube. A tool designed in this way will have the same advantages as described earlier in relation to the torsion wire, i.e. when rotating the second handle piece in relation to the first handle piece, the torsion wire will function as a torque limiter, by engagement of the yoke in the grooves and ridges of the internal cavity, when rotated for extending the helix from the tip of the cardiac stimulator lead and hence attaching it to the heart wall. The torsion wire will also function as a pressure limiter by being displaceable in the longitudinal direction due to deformation of the elastic yoke. A further advantage with this tool is that by rotating of the first handle piece in relation to the second handle piece, the tip of the cardiac stimulator lead can be pivoted and hence guided to the desired position inside the heart. When the tip is located in the desired location, it can be hold in position by means of the first handle piece while the helix being screwed out from the tip by rotating the second handle piece.

It should be understood that the tool may be designed in many different ways within the scope of the associated claims, and is thus not limited to the embodiments disclosed in the following examples. The handle, for example, may have different form and need not be completely closed. It is sufficient that it has an internal cavity, with a corrugated circumferential boundary surface, and some structure guiding and supporting the torsion wire and, if applicable, the guide tube, on the distal side of the cavity, as well as a structure supporting the torsion wire on the proximal side of the cavity. The cavity itself is in the drawings illustrated with a circular cylindrical form. However, it could also adapt other forms, e.g. spherical, part spherical or having an oval form in longitudinal section.

DESCRIPTION OF THE PREFERRED EMBODIMENTS

Figure 1:
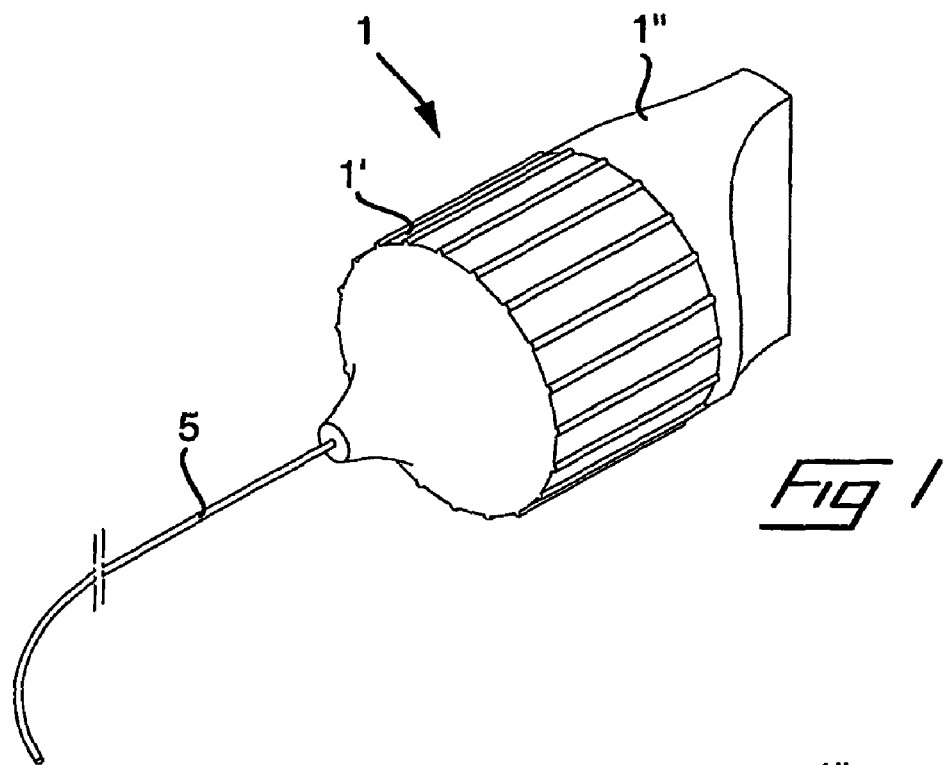
FIG. 1 is a perspective view of a tool according to the invention in a first embodiment.
Figure 2:
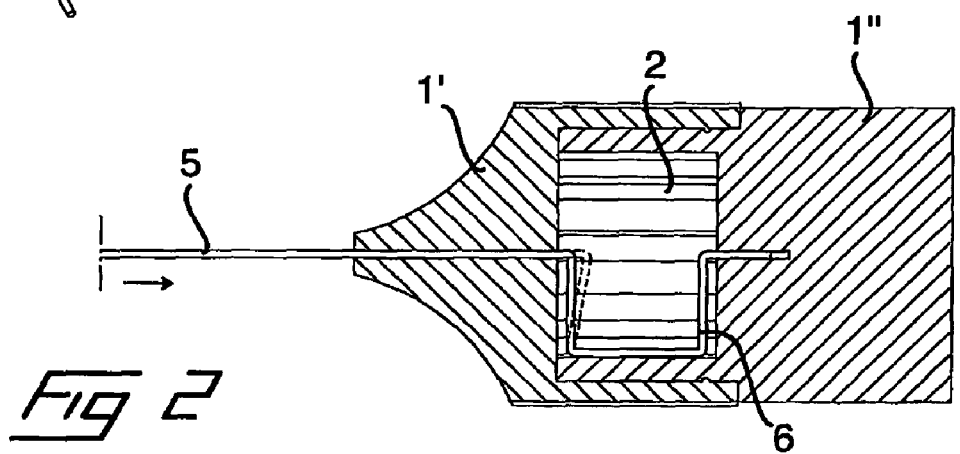
FIG. 2 is a longitudinal section of the tool shown in FIG. 1.

Reference is first made to FIGS. 1 and 2 in which a first embodiment of a tool according to the invention is illustrated in a perspective view and a longitudinal section, respectively. The tool comprises a handle 1 of a general cylindrical shape. The handle is assembled of a first handle piece 1' and a second handle piece 1", wherein a portion of the second handle piece is inserted into the first handle piece. A cylindrical recess is provided in the second handle piece, such that in an assembled state, the two handle pieces will define an internal cavity 2. The cavity has a general circular cross section, as is seen from FIG. 3, but is provided with grooves 3 and ridges 4 in the longitudinal direction of the envelope surface or circumferential boundary surface of the cylindrical cavity.

A bore is provided in the first handle piece 1', which is forming the distal end or side of the cavity, as well as in the second handle piece 1", which is forming the proximal end or side of the cavity. Both of these bores are located in an imaginary extension of a centre line or axis of the cylindrical cavity. A proximal portion of a torsion wire 5 is inserted into the bores and is rotationally supported in both the first and the second handle piece. The portion of the torsion wire which is extended through the cavity 2, is resilient and formed as a U-shaped yoke 6. The bottom part of the U-shaped yoke 6 is in engagement with the grooves 3 and the ridges 4 at the circumferential boundary surface of the cavity. To facilitate positioning of the yoke 6 in the cavity 2, this is preferably done with the first and second handle pieces in a separated state, after which the handle pieces are assembled. However, in this embodiment the first and second handle pieces are preferably not rotatable in relation to each other in the assembled state.

Figure 3:
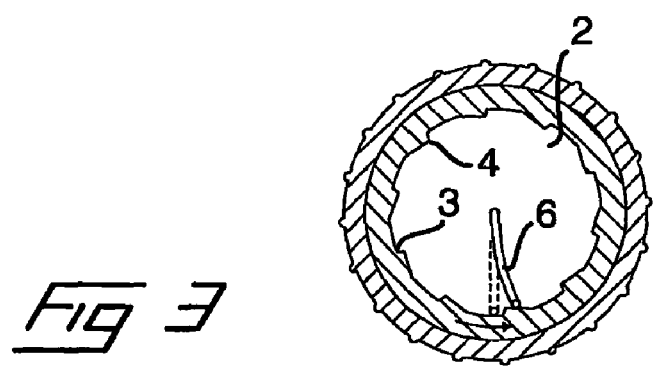
FIG. 3 is a cross-section of the tool shown in FIG. 1, illustrating the deformation and displacement of the yoke when functioning as a torque limiter.
Figure 4:
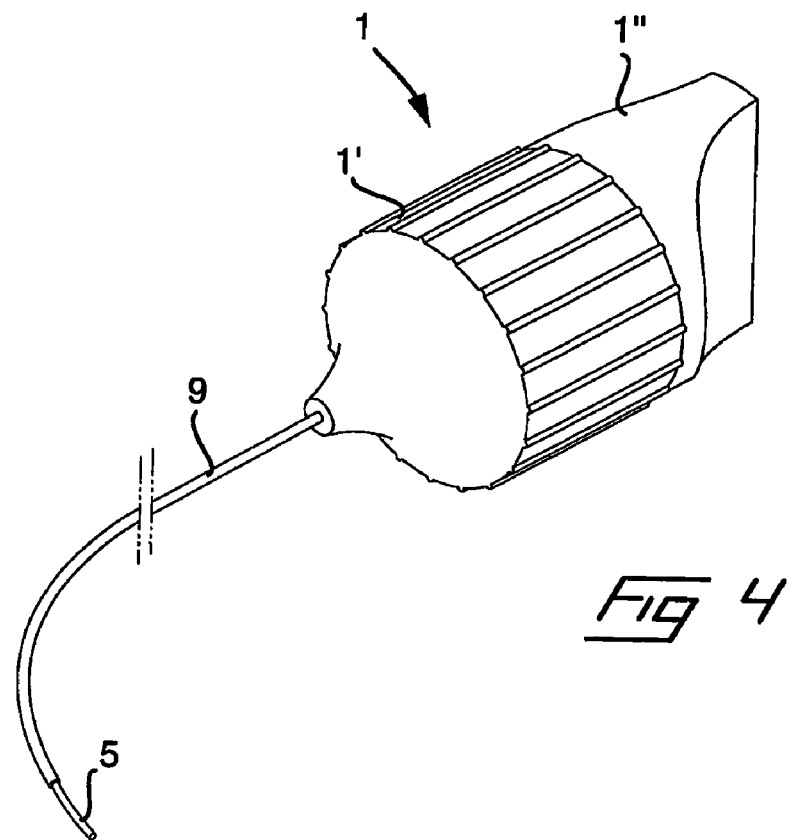
FIG. 4 is a perspective view of the tool in accordance with the invention in a second embodiment.
Figure 5:
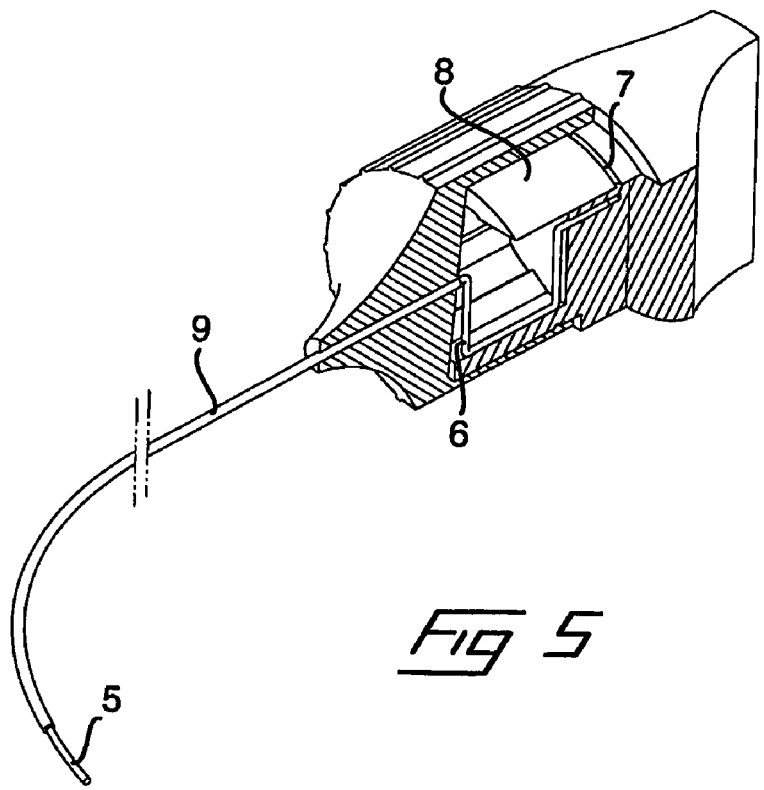
FIG. 5 is a partially sectioned perspective view of the tool shown in FIG. 4.
Figure 6:
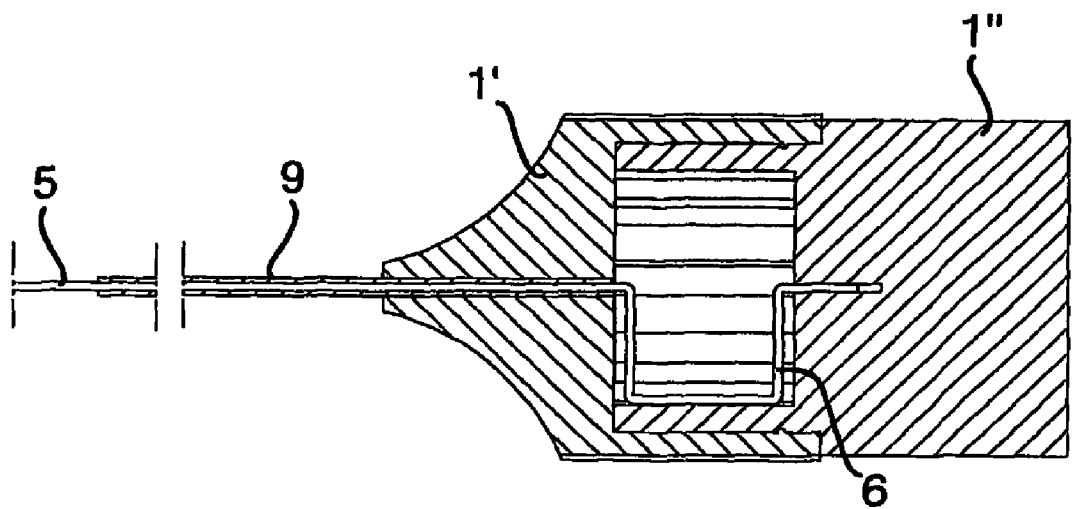
FIG. 6 is a longitudinal section through the tool shown in FIG. 4.

The torsion wire 5 is in a distal end (not shown here) provided with an engagement formation, for engagement with a mating engagement formation at a proximal end of a helix or operating member in the tip of a cardiac stimulator lead, as will be shown and described in more detail hereinafter. By rotating the torsion wire 5, the helix can be screwed out to an extended position such that it penetrates into a heart wall for attaching of the lead inside the heart. When performing this screwing or rotating action of the torsion wire, the handle 1 is rotated, as is illustrated by an arrow in FIG. 3. Since the yoke is in engagement with one of the grooves in the outer circumference of the cavity, also the torsion wire 5 will then be rotated. However, if the torque applied to the handle is large enough, the yoke will be deformed, as is illustrated in FIG. 3 and if the applied torque exceeds a predetermined torque limit, the yoke eventually will ratch over the intermediate ridge 4 into the subsequent groove 3, as is illustrated by broken lines in FIG. 3. Accordingly, as long as the torque is beyond the torque limit, no further rotation of the torsion wire may be performed since the yoke will only rotate in relation to the handle. As can be seen from FIG. 3, the ridges have a sloping surface in the direction of rotation of the handle when screwing out or extending the helix, whereas the opposite surfaces of the ridges are steeper and can thus transmit a higher torque when screwing in or retracting the helix, i.e. when detaching the cardiac stimulator lead from the heart wall.

In FIG. 2 is illustrated another advantageous feature according to a further aspect of the invention. Namely, by providing the torsion wire displaceable in the longitudinal direction in the first handle piece, the torsion wire is prevented from transmitting too large pressure force in the longitudinal direction. When the pressure force become too large, the yoke 6 will be deformed, as is illustrated by broken lines. By this the risk of accidentally pressing a cardiac stimulator lead into the heart wall is eliminated, a risk which is a reality with decreasing cross sectional dimensions of the cardiac stimulator leads.

Now reference is made to FIGS. 4-7 in which is disclosed another embodiment according to a further aspect of the invention. This embodiment presents many similarities in comparison to the described embodiment in FIGS. 1-3. Accordingly, this embodiment has a handle 1, assembled from a first handle piece 1' and a second handle piece 1" which are assembled together. One prerequisite for this embodiment, is however that the first and the second handle pieces 1', 1" are rotatable in relation to each other, for reasons which will be explained below. The rotational feature in combination with a safe assembling, may be achieved by e.g. providing the first handle piece 1' with a circumferential ridge on the inside, which will engage a circumferential groove 7 on the outside of a portion 8 of the second handle piece 1", which is inserted into the fast handle piece. In the second handle piece is formed a cylindrical recess which in an assembled state will define an internal cavity 2 having a circumferential or envelop surface provided with grooves 3 and ridges 4.

In this embodiment is also provided a guide tube 9, a proximal end of which is inserted into the bore, being coaxial with the center axis of the cavity 2, in the first handle piece 1' and is securely mounted in a torsion resistant way therein. The torsion wire 5 is in this case inserted through the bore defined by the guide tube 9 in the first handle piece 1' and is rotatable supported as well as longitudinally displaceable in that bore. In the second handle piece 1" the torsion wire is, as in the previous embodiment, inserted in the bore therein, which also is coaxial with the centre axis of the cavity, and is at least rotatable supported therein. The intermediary portion of the torsion wire is formed with a yoke 6 in the area of the cavity 2.

Figure 7:
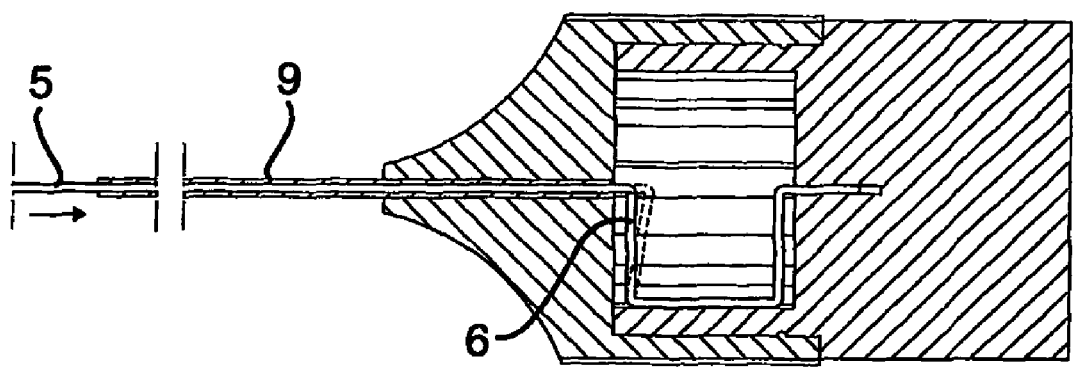
FIG. 7 is a longitudinal section corresponding to that of FIG. 6, illustrating the deformation of the yoke when functioning as a pressure limiter.

Accordingly, the tool will have a torque limiting function for the torsion wire when rotating the second handle piece 1", due to the deformation and ratching of the yoke 6 from one groove 3 over intermediate ridges 4 into subsequent grooves, in a similar way as the first embodiment which is described in connection to FIG. 3. The tool will also have a pressure limiting function, in a similar way as described with reference to the previous embodiment. This is illustrated in FIG. 7 where it is indicated with broken lines how the torsion wire 5 may slide and deform inside the bore of the guide tube 9, when the handle is pressed toward the distal end of the torsion wire with a force exceeding the elasticity in the yoke 6.

Figure 8:
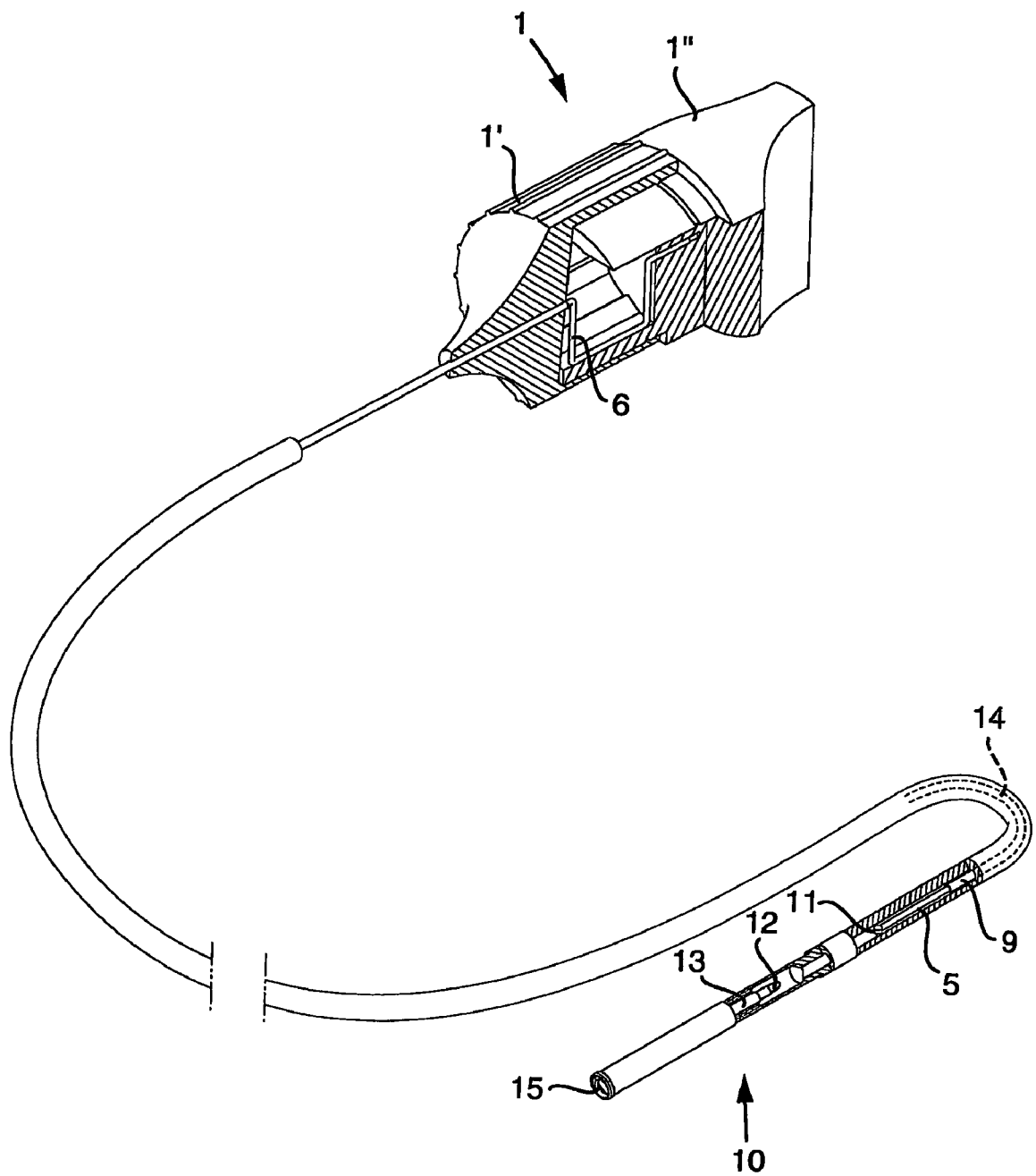
FIG. 8 is a perspective view of the complete tool according to the second embodiment interacting with a cardiac stimulator lead, the tip of which is partially sectioned.

Referring now to FIG. 8 in which is shown a partly cut through perspective view of a complete tool, according to the second embodiment of the invention. In the drawing is indicated the use of the tool for guiding and attaching of a cardiac stimulator leadhaving a tip 10 in its distal end. In reality, the cardiac stimulator has nearly the same length as the torsion wire 5 and the guide tube 9 of the tool, and is preferably inserted through a vein, e.g. in the area of a patient's shoulder, and pushed through the vein until the tip 10 is located inside the heart. When the tip is inside the heart, the torsion wire 5 and the guide tube 9 is inserted into a bore, which is provided in the cardiac stimulator lead, until the torsion wire and the guide tube is in the area of the tip 10. As is indicated in the drawing, the distal end of the torsion wire is provided with an engagement formation 11 which is adapted to engage a mating engagement formation 12 in a proximal end of an operating member 13 in the tip 10. The operating member 13 is connected to a helix (not shown) located in the tip. In the drawing is also indicated that the guide tube 9 is formed with a preformed, curved portion 14 in the vicinity of its distal end. The guide tube 9 has resilient characteristics, such that the curved portion 14 may straighten out when inserted through the vein and cardiac stimulator lead, and subsequently recover its initial shape when it arrives inside the heart.

When the tool, according to the above described second embodiment, is used for positioning and attaching of a cardiac stimulator lead inside a heart, the following steps may preferably be carried out. Firstly, the cardiac stimulator lead is inserted through a vein until the tip 10 is located inside the heart. The cardiac stimulator lead is preferably inserted without the guide tube 9, or with another straight stiffening wire, to prevent that the curve 14 should obstruct the insertion. When the cardiac stimulator lead is in place, the torsion wire 5 and the guide tube is inserted through the bore in the cardiac stimulator lead until the distal ends of the torsion wire and the guide tube have reached the tip 10. Preferably, the torsion wire is inserted so far such that the engagement formation 11 goes into engagement with the engagement formation 12 on the operating member 13. The pressure limiting feature due to the deformation of the yoke 6, as described earlier, will prevent the application of any injurious pressure force in the longitudinal direction when inserting the torsion wire. In this state, the tip 10 of the cardiac stimulator lead may be guided to the desired position inside the heart with the distal end of the cardiac stimulator lead bearing against the inside surface of the heart wall. This can be accomplished by rotating the first handle piece 1' which in its turn will rotate the guide tube 9 and, due to the curved portion 14 in the distal end of the guide tube, this will cause a pivoting of the tip 10. When the desired position of the tip 10 has been reached, the tip can be hold in this state by holding the first handle piece 1' immovable during rotation of the second handle piece 1". By doing so, the torsion wire 5 and the operating member 13 will be rotated which will affect the helix to be screwed out from an aperture 15 in the distal end of the tip 10, to an extended position. Accordingly, the helix will penetrate into the heart wall and attach the cardiac stimulator lead thereto. The torque limiting feature due to the deformation and ratching over of the yoke 6 from groove to groove, will prevent the transmitting of a too large torque to the helix and the possibility that the helix should draw the tip of the cardiac stimulator lead into the heart wall and injure it, due to twisting of the entire cardiac stimulator lead after a possible helix stopper has been reached.

The tool according to the first embodiment of the invention, which has been described in relation to FIGS. 1-3, can be used in a corresponding way as has been described hereinabove in relation to FIG. 8. However, the first embodiment does not have any guide tube 9 and accordingly, the tip of the cardiac stimulator lead can not be guided by pivoting it, as described above. There is thus no meaning in having a handle in which the two handle pieces 1', 1" are rotatable in relation to each other, but instead the handle pieces are preferably immovable attached to each other. However, the torsion wire 5 can be operated in a similar way, by means of the immovable assembled handle 1, and has the same features as described above, i.e. the pressure limiting and the torque limiting features.

Although modifications and changes may be suggested by those skilled in the art, it is the intention of the inventors to embody within the patent warranted heron all changes and modifications as reasonably and properly come within the scope of their contribution to the art.

The invention claimed is:

1. A tool for attaching a cardiac stimulator lead at a desired position inside a heart, the stimulator lead being formed as a flexible tube comprising electrical conductors and a helix, which is extendable out of a distal end of the tube by a screw rotating motion for penetration into and attachment at the desired position, and having a proximal end interconnected with an operating member, the tool comprising:
  a flexible torsion wire, having an engagement formation in a distal end thereof, and being configured for insertion into the cardiac stimulator lead to produce the screw rotating motion of the operating member by rotating the torsion wire when the engagement formation in the distal end of the torsion wire is in engagement with a mating engagement formation in a proximal end of the operating member;
  the tool further comprising a rotatable handle having an internal cavity therein having a proximal side an a distal side with a generally circular form in cross section perpendicular to a center axis, between the proximal side and the distal side of the cavity, the internal cavity being corrugated in a circumferential boundary surface thereof between said proximal side and said distal side, having grooves and ridges parallel to the center axis, a proximal portion of the flexible torsion wire proceeding through the proximal side and extending into the distal side of the internal cavity coaxially with the center axis of the internal cavity, said torsion wire being freely in said proximal side and said distal side and having a non-coaxial, resilient yoke formed portion in the internal cavity with at least a part of the yoke in contact and engagement with the grooves and ridges of the circumferential boundary surface to produce rotation of said torsion wire with said boundary surface when said handle is rotated, wherein when the torque applied to said handle exceeds a predetermined torque limit, said part of the yoke in contact and engagement with any one of the grooves will slide out engagement with the groove.

2. A tool according to claim 1, wherein the torsion wire is supported displaceable in the longitudinal direction in the distal end of the internal cavity.

3. A tool according to claim 1, wherein the ridges in the circumferential boundary surface of the internal cavity being generally saw tooth-shaped in cross section, having a sloping surface in the direction of extending the helix, and a more steep opposite surface.

4. A tool according to claim 1, wherein the handle comprises a first handle piece and a second handle piece, which are rotatable in relation to each other, and wherein a proximal end of a resilient guide tube, having a preformed curved portion at a distal end, is torsion resistant attached in a bore in the first handle piece, and the torsion wire is supported rotatable and displaceable in the longitudinal direction in a bore in the guide tube, the guide tube being insertable into a bore of the cardiac stimulator lead.

* * * * *